US00RE37357B1

(19) United States
(12) Reissued Patent
Lynn

(10) Patent Number: US RE37,357 E
(45) Date of Reissued Patent: Sep. 4, 2001

(54) LUER-RECEIVING MEDICAL VALVE AND FLUID TRANSFER METHOD

(76) Inventor: Lawrence A. Lynn, 862 Curleys Ct., Worthington, OH (US) 43235

(21) Appl. No.: 09/140,413

(22) Filed: Aug. 26, 1998

Related U.S. Patent Documents

Reissue of:
(64) Patent No.: 5,549,651
Issued: Aug. 27, 1996
Appl. No.: 08/248,646
Filed: May 25, 1994

(51) Int. Cl.[7] ..... A61M 39/00
(52) U.S. Cl. ..... 604/533; 604/33; 604/169; 251/334
(58) Field of Search ..... 604/33, 169, 231, 604/236, 246, 249, 256, 905, 244, 167, 533, 537; 251/149.1, 149

(56) References Cited

U.S. PATENT DOCUMENTS

| | | | | |
|---|---|---|---|---|
| 2,546,672 | | 3/1951 | Clair . | |
| 3,577,992 | | 5/1971 | Merry . | |
| 3,659,587 | * | 5/1972 | Baldwin | 128/2 |
| 3,986,508 | * | 10/1976 | Barrington | 128/214.2 |
| 4,197,848 | * | 4/1980 | Garret et al. | 128/247 |
| 4,214,779 | * | 7/1980 | Losell | 285/93 |
| 4,496,350 | * | 1/1985 | Cosentino | 604/175 |
| 4,511,359 | * | 4/1985 | Vaillancourt | 604/411 |
| 4,685,654 | * | 8/1987 | Hu | 251/205 |
| 4,758,225 | * | 7/1988 | Cox et al. | 604/126 |
| 4,763,648 | * | 8/1988 | Wyatt | 128/673 |
| 4,768,568 | * | 9/1988 | Fournier et al. | 141/286 |
| 4,809,679 | * | 3/1989 | Shimonaka et al. | 128/4 |
| 4,834,152 | * | 5/1989 | Howson et al. | 141/286 |
| 4,929,235 | * | 5/1990 | Merry et al. | 604/167 |
| 4,950,257 | * | 8/1990 | Hibbs et al. | 604/265 |
| 4,981,469 | * | 1/1991 | Whitehouse et al. | 604/86 |
| 4,998,927 | * | 3/1991 | Vaillancourt | 604/283 |
| 5,100,394 | | 3/1992 | Dudar . | |
| 5,108,380 | * | 4/1992 | Herlitze et al. | 604/283 |
| 5,114,400 | * | 5/1992 | Lynn | 604/53 |
| 5,147,305 | * | 9/1992 | Nakamura . | |
| 5,149,327 | * | 9/1992 | Oshiyama . | |
| 5,178,607 | * | 1/1993 | Lynn et al. | 604/86 |

(List continued on next page.)

FOREIGN PATENT DOCUMENTS

| | | | |
|---|---|---|---|
| 90/11103 | * | 10/1990 | (WO) . |
| PCT 98/52631 | | 11/1998 | (WO) . |

OTHER PUBLICATIONS

Brochure by McGaw, The Clave™ IV Administration System.*
Sample of Buron One–Way Valve System.*

*Primary Examiner*—Corrine McDermott
*Assistant Examiner*—Cris L. Rodriguez
(74) *Attorney, Agent, or Firm*—Nixon & Vanderhye PC

(57) ABSTRACT

A medical valve is provided that includes a housing having a main conduit and a branch extending from the main conduit and in fluid communication with it. The bore of the branch has an elastomeric septum piston disposed therewithin and at least a portion of the elastomeric septum piston is movable by either compression or by a longitudinal advancement along the secondary bore towards the bore of the main conduit. In one embodiment, the septum piston is cylindrical and includes a centrally positioned slit. The bore of the branch includes two opposing projecting members along a distal portion of the bore which effectively narrow the diameter of the bore. When the elastomeric member is pushed from a proximal position to a distal position, it is transversely compressed by the projecting members to open the slit and allow fluid passage. After removal of the longitudinal displacement force the septum piston retracts away from the distal portion back to the proximal portion.

40 Claims, 5 Drawing Sheets

U.S. PATENT DOCUMENTS

| | | | | |
|---|---|---|---|---|
| 5,199,948 | | 4/1993 | McPhee . | |
| 5,201,725 | * | 4/1993 | Kling . | |
| 5,211,370 | * | 5/1993 | Powers . | |
| 5,211,638 | | 5/1993 | Dudar . | |
| 5,215,537 | * | 6/1993 | Lynn et al. | 604/244 |
| 5,215,538 | * | 6/1993 | Larkin . | |
| 5,221,271 | * | 6/1993 | Nicholson et al. | 604/283 |
| 5,242,432 | * | 9/1993 | De Frank . | |
| 5,251,873 | * | 10/1993 | Atkinson . | |
| 5,273,533 | * | 12/1993 | Bonaldo . | |
| 5,295,657 | | 3/1994 | Atkinson . | |
| 5,295,658 | | 3/1994 | Atkinson . | |
| 5,300,034 | | 4/1994 | Behnke . | |
| 5,356,396 | * | 10/1994 | Wyatt et al. | 604/283 |
| 5,360,413 | * | 11/1994 | Leason . | |
| 5,390,898 | * | 2/1995 | Smedley et al. | 251/149.6 |
| 5,396,925 | * | 3/1995 | Poli | 137/493 |
| 5,402,982 | | 4/1995 | Atkinson . | |
| 5,403,293 | | 4/1995 | Grabenkort . | |
| 5,405,331 | | 4/1995 | Behnke . | |
| 5,417,673 | * | 5/1995 | Gordon | 604/283 |
| 5,441,487 | * | 8/1995 | Vedder | 604/167 |
| 5,449,145 | * | 9/1995 | Wortrich | 251/322 |
| 5,466,219 | | 11/1995 | Lynn . | |
| 5,474,544 | * | 12/1995 | Lynn | 604/283 |
| 5,501,426 | | 3/1996 | Atkinson . | |
| 5,533,708 | | 7/1996 | Atkinson . | |
| 5,603,706 | | 2/1997 | Wyatt . | |
| 5,632,735 | | 5/1997 | Wyatt . | |
| 5,694,686 | | 12/1997 | Lopez . | |
| 5,697,915 | | 12/1997 | Lynn . | |
| 5,699,821 | | 12/1997 | Paradis . | |
| 5,749,861 | * | 5/1998 | Guala et al. | 604/249 |
| 5,797,897 | | 8/1998 | Jepson . | |
| 5,820,601 | * | 10/1998 | Mayer | 604/167 |
| 5,871,500 | | 2/1999 | Jepson . | |

* cited by examiner

LUER-RECEIVING MEDICAL VALVE AND FLUID TRANSFER METHOD

Matter enclosed in heavy brackets [ ] appears in the original patent but forms no part of this reissue specification; matter printed in italics indicates the additions made by reissue.

*More than one application for Reissue of U.S. Pat. No. 5,549,651 has been filed. This Reissue Application is the parent of Continuation Reissue Application No. 09/699,398 Oct. 31, 2000.*

BACKGROUND AND SUMMARY OF THE INVENTION

The risk of needlestick injury and the expense associated with accessory cannulae, whether blunt or sharp, are well known. Conventional intravenous tubing systems utilize tapering luer male cannula connectors, often within an associated surrounding threadable member defining a luer-lock connector commonly used for achieving tight, sustained connections. A bare luer taper cannula without the associated threadable member is commonly called a luer slip connector and is widely utilized for brief prn injections. Both of these luer systems are in wide use throughout conventional hospital systems and it would be preferable to develop a connecting valve system which receives and is activated by conventional luer slip tapers or luer lock tapers so that incorporation into existing hospital systems is rapid and associated with minimal cost. It would be advantageous for such systems to avoid deadspace so that the surface could be easily wiped with antiseptic to avoid the need for capping after each use. Furthermore, the elimination of deadspace allows for the aspiration of blood through such systems without the collection of blood within the deadspace. Another important feature of such systems is the minimization of "kickback"—that is, it is important that the luer slip tip or luer lock systems, when not tightly locked, do not kickback out of the valve, thereby producing the potential for a spurt of blood or fluid into the environment and potential contamination of the operator. The prior art includes several luer-receiving valves which do not have substantial deadspace. U.S. Pat. No. 5,201,725 discloses shows a valve which utilizes an elastomeric member which opens by force induced by a threadable member over the elastomeric septum piston. Such a system will not work with a conventional luer lock system since the male taper extends centrally adjacent the luer lock threading member and therefore, it would not be possible to compress the septum piston within the luer-lock threads in such a system without inserting the male member itself into the septum piston. The background discussed in the aforementioned patent provides additional background for the present invention.

A device, designated the CLAVE™, for an injection port marketed by McCaw, is included in the Prior Art. This device utilizes a cannula surrounded by a septum piston. The septum piston is compressed by the luer taper, thereby allowing the needle and its associated bore to enter the bore of the luer taper, thereby opening fluid communication. However, such systems would be expected to be associated with substantial kickback when used with a luer slip system since the septum piston must be relatively resilient to prevent leakage associated with higher fluid pressures within the cannula. Further, the requirement of a spike or cannula within the bore of the valve results in considerable increase in expense associated with complex insert molding of the device. It is, therefore, preferable to develop a more simplified valve system which can receive a luer taper cannula and which eliminates the need for complex insert molding to minimize the potential for kickback and the potential for trapped fluid or blood while still providing a deadspace-free surface which can be easily wiped with antiseptic.

In general, the present invention comprises a housing including a main conduit having a main bore and further having a branch extending away from the main conduit and including a secondary bore extending through the branch in fluid communication with the main conduit. The secondary bore may be aligned directly with the main conduit or may branch from the main conduit. The main conduit may, for example, comprise a catheter or may be a primary intravenous tubing system or arterial line. The secondary bore defines a longitudinal axis. An elastomeric septum piston is disposed within the secondary bore and at least a portion of the elastomeric septum piston is moveable by either compression or by longitudinal advancement along the secondary bore toward the main bore. In one preferred embodiment, the septum piston is cylindrical and includes a centrally positioned slit extending along the longitudinal axis of the cylindrical septum piston. The cylinder includes a proximal end and a distal end. The proximal end preferably extends to a position adjacent the proximal end of the secondary bore so that the surface of the proximal end of the septum piston is easily accessible adjacent the proximal end of the branch and therefore can be easily wiped with antiseptic. This is an important feature since it eliminates the need for capping after blood aspiration or drug injection. The bore of the secondary branch preferably includes two opposing projecting members along a distal portion of the bore which effectively narrow the diameter of the bore along at least a portion of one longitudinal axis. In the preferred embodiment, the central slit through the septum piston defines a longitudinal axis transverse to the longitudinal axis of the septum piston. With this embodiment, the longitudinal plane of the narrowed distal portion of the secondary bore is aligned with the longitudinal axis of the slit through the elastomeric septum piston. Furthermore, the elastomeric septum piston is sized to be transversely compressed by the projecting distal portions of the secondary bore. Since the slit is aligned with the projecting portions, transverse compression of the septum piston occurs along an axis which corresponds with the longitudinal axis of the slit so that when the elastomeric member is pushed from a proximal position into a distal position, the elastomeric member is transversely compressed by the projecting portions along the distal secondary bore, the compression causing the formerly tightly-closed slit to shorten and thereby open, allowing fluid to pass through a nascent flow channel formed by the shortened slit through the elastomeric septum piston. When the septum piston retracts away from the distal portion back into the proximal portion, the slit returns to its tightly closed position, thereby occluding further fluid communication through the septum piston.

In the preferred embodiment, the projecting portions progressively lengthen to define a progressively decreasing distance between the projecting members so that the projecting members are closer to one another adjacent the main bore than adjacent the proximal cylindrical portion of the secondary bore. This effectuates a progressive enlargement of the opening through slit of the elastomeric septum piston when the elastomeric septum piston is fully advanced into the proximal portion of the secondary bore. Furthermore, after removal of the luer, as the elastomeric septum piston retracts away from the distal compressing portion toward the proximal portion, the slit progressively closes from its proximal extent toward its distal extent, thereby expressing fluid toward the main bore rather than toward the proximal opening of the secondary bore. This reduces the chance of blood or fluid refluxing out of the septum piston into the environment or into the secondary bore when luer taper cannula is withdrawn from the secondary bore. The branch of the main conduit can be aligned directly with or perpendicular to the main conduit or can be at an oblique or acute angle with the main conduit. The main conduit is generally discussed below as integral with the valve, but the main conduit may be a separate piece and sold separately, and may be joined with the branch or the aligned secondary bore by a threadable member as ,for example, joining a conventional heparin well or prn adapter to a catheter, stopcock, or IV tubing system. The branch preferably includes at least one external thread or thread receiver for receiving an internal female threading member to allow a secure threaded connection with a conventional luer-lock type connector of the type commonly used with conventional syringes or intravenous tubing systems. The use of this luer-activated valve in association with IV piggyback administration generally would require the recapping of the luer taper after use so that the luer taper remains sterile between IV piggyback mediation administrations. My U.S. Pat. No. 5,167,643 (the disclosure of which is hereby incorporated by reference as if completely disclosed herein) describes a Docking Station for receiving a blunt cannula such as a tapered luer end to maintain the sterility of the tapered end. The present invention includes the secondary tubing system having a docking station intended for use with a conventional luer taper cannula of the slip tip or luer lock type. This station utilizes a simple membranous cover since the primary function of the cover is to cover and seal the luer within the station, as discussed in the previous patent. The new protection station may include an annular shield for protecting the fingertips against inadvertent contact of the luer taper since the luer taper has been removed from fluid connection with the patient's blood vessel and, therefore, could be contaminated by potentially infectious material which, by even surface contamination of a nurses fingers, could subsequently enter a fissure in the fingers or otherwise be transferred to a mucous membrane where infection could ensue. The station preferably includes a connecting portion for connecting to a proximal portion of the intravenous piggyback system or supporting pole, as described in my aforementioned patent. The combination of a primary fluid system which incorporates a luer-activated valve and a secondary system which incorporates a luer cannula protection station which protects the tapered blunt cannula of the luer provides reliable intermittent connection to the patient with assurance that the luer taper remains sterile between use and eliminates the need for the utilization of multiple caps, thereby reducing overall cost.

It is the purpose of the present invention to provide an inexpensive medical valve which can be activated by a conventional luer taper cannula and thereby be widely implemented within existing hospital systems.

It is further the purpose of this invention to provide a medical valve which can be easily wiped with antiseptic to eliminate the need for recapping after use. It is further the purpose of this invention to provide a medical valve having substantially no deadspace adjacent its proximal portion to eliminate the pooling of blood or liquid within the valve so that the valve may be repetitively used for the aspiration of blood and reinjection of liquids. It is further the purpose of this invention to provide a luer-activated opening of a central fluid path which is automatically aligned with the bore of the luer and which will directly communicate with the bore of a luer taper cannula upon the transmission of longitudinal force of the luer taper cannula against the septum piston, thereby providing a mechanism for the opening of a centrally-positioned fluid path at the same time tight sealing occurs adjacent the distal end of the luer taper cannula against the septum piston. It is further the purpose of this invention to provide a valve which progressively closes from its proximal extent to its distal extent, thereby expressing residual fluid from the valve away from the environment. It is further the purpose of this invention to provide a two-piece valve which can be simply manufactured by the insertion of an elastomeric septum piston into a rigid tubular structure, thereby avoiding the need for expensive and complex insert molding.

These and other features will become evident from the summary and detailed description described below. Furthermore, these and other objects and advantages of the invention will be further set forth in the description which follows and, in part, will be learned from the description or may be learned by practice of the invention. The objects and advantages of the invention may be realized by means of the instrumentalities and combinations particularly pointed out in the appended claims.

DESCRIPTION OF THE PRESENTLY PREFERRED EMBODIMENTS

Figure 1:
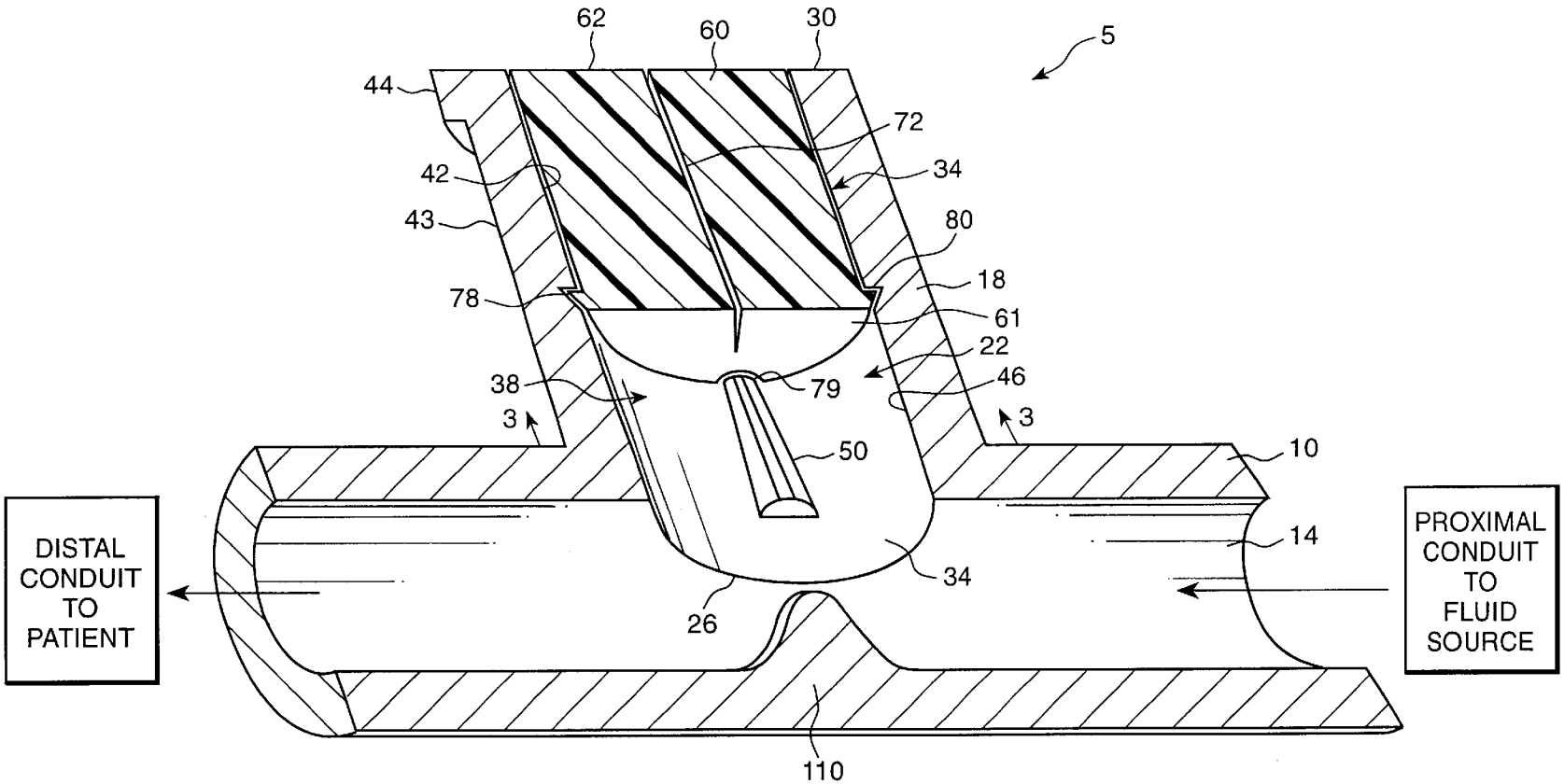
FIG. 1 is a partial perspective view of a longitudinal section of the luer-receiving valve with the piston septum being in its resting detented position.
Figure 2:
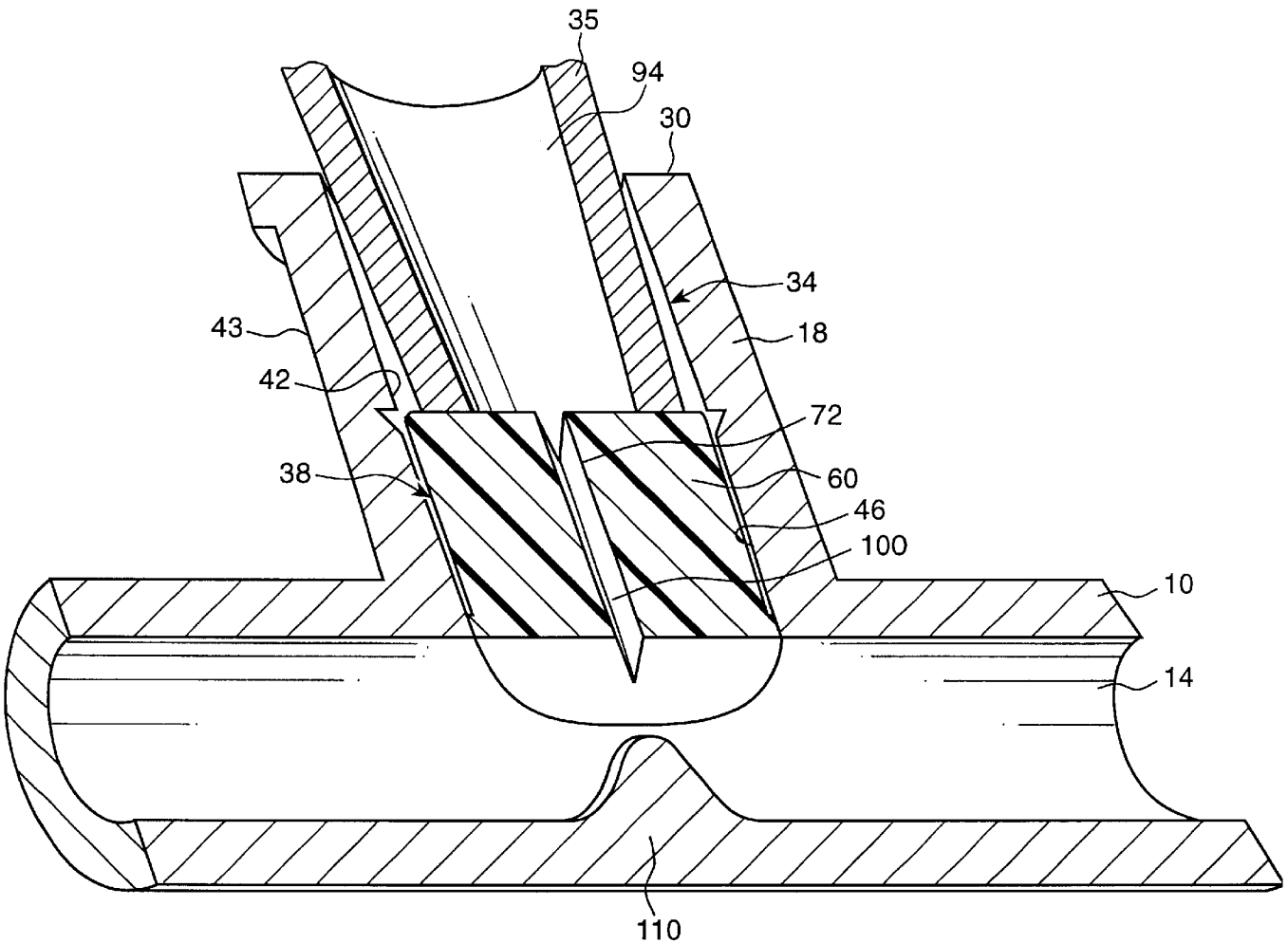
FIG. 2 is a partial perspective view of a longitudinal section of the luer-receiving valve with the blunt luer taper cannula of the conventional slip-tip type fully inserted into the cylinder.
Figure 3:
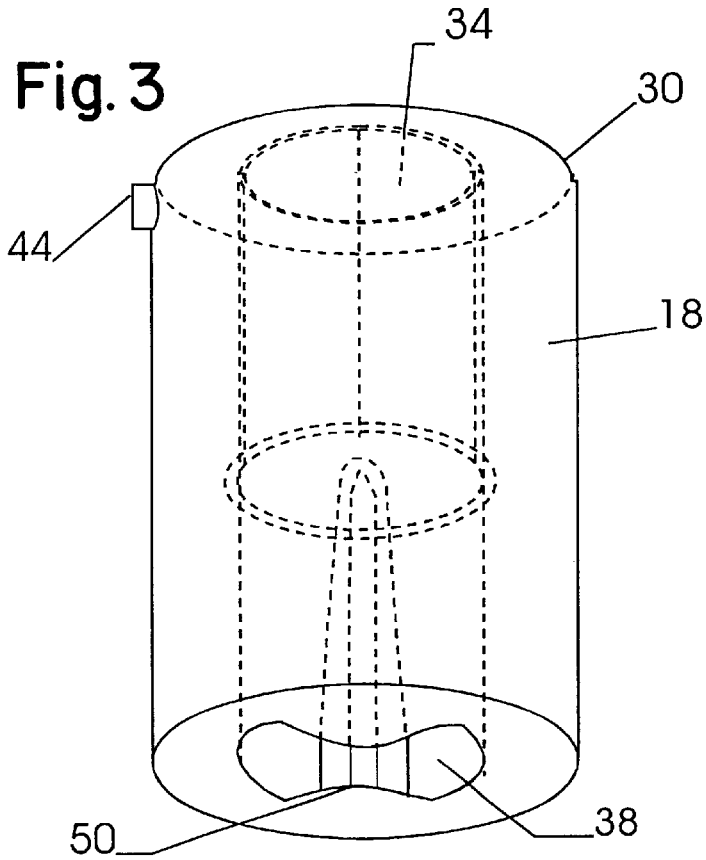
FIG. 3 is a perspective view of a section through lines 3.3 of FIG. 1.
Figure 4:
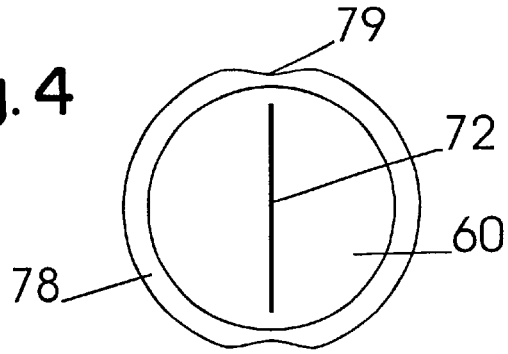
FIG. 4 is a top view of the septum piston in its resting state.

The luer tapered cannula receiving valve 5 (FIG. 1) includes a main conduit housing 10 having a main bore 14 and a secondary branch or cylinder 18 having a secondary bore 22. The cylinder 18 includes a distal end 26 adjacent the main bore 10 and a proximal end 30. The cylinder 18 further includes a cylindrical proximal bore portion 34 sized to sealingly receive a conventional tapered luer male cannula 35 (as shown in FIG. 2) and distal bore portion 38. The proximal bore portion 34 is defined by inner cylindrical walls 42 and outer walls 43 and includes outer thread receiving post 44 adjacent the proximal end 30 (although complete outer threads may be provided). A distal bore portion 38 is defined by distal wall 46 having opposing projecting members 50 which effectively narrow the transverse width of the distal bore portion 38 along a longitudinal plane through the opposing projecting members 50 (as best shown in FIG. 3). A cylindrical elastomeric septum piston 60 having a distal end 61 and a proximal end 62 is provided and includes a centrally positioned slit 72 extending from the proximal end 62 to the distal end 61 which can, if desired, receive a steel blunt cannula or sharp needle (not shown). The elastomeric septum piston 60 can be comprised, for example, of silicone rubber or of latex rubber and is both resilient and compressible. The septum piston 60 is preferably sized to be tightly received within the cylindrical proximal bore portion 34 so as to effectively sealingly wipe the cylindrical side walls 42 of the proximal bore portion 34 upon movement of the proximal end 62 of the septum piston 60 back toward the proximal end 30 of the cylinder 22, as will be discussed.

In the preferred embodiment, a silicone lubricant is provided to enhance the sliding piston-like action of the sealingly received septum piston 60 against the side walls 42 and 46 of the cylinder 18. As noted previously, the slit 72 extends completely through the cylindrical septum piston 60. The long transverse axis of the slit 72 (in the transverse plane of the septum piston) is aligned within the same plane as the longitudinal axis through the opposing projecting members 50 of the distal bore portion 38 (FIG. 1). Furthermore, the transverse diameter of the distal bore portion along an axis perpendicular to the longitudinal plane of the projecting members 50 can be slightly greater than the transverse diameter of the septum piston 60 to thereby, during operation, receive a bulging portion of the septum piston 60, as will be discussed.

A septum wiper 78 is provided and a bore detent 80 is provided to retain the elastomeric septum piston 60 within the secondary bore by receiving the septum wiper. The wiper 78 is flexible to provide a tight seal. A second wiper (not shown) can be provided adjacent the proximal end 62 to provide additional sealing. The wiper 78 includes a partial recess 79 for receiving the projecting members 50 to allow tight sealing when passing over the members 50. After insertion, during manufacture, the septum detent wiper 78 engages the detent 80. As shown, the septum wiper 78 is configured so as to allow distal displacement of the septum piston 60 out of its detented position (of FIG. 1), but to prevent proximal bore displacement of the septum piston 60 out of its detented position.

Figure 5:
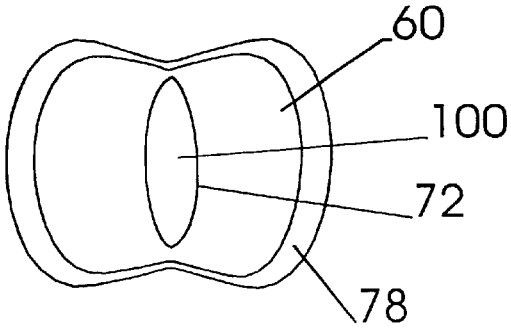
FIG. 5 is a top view of the septum piston in its fully advanced compressed state, showing the open slit.
Figure 6:
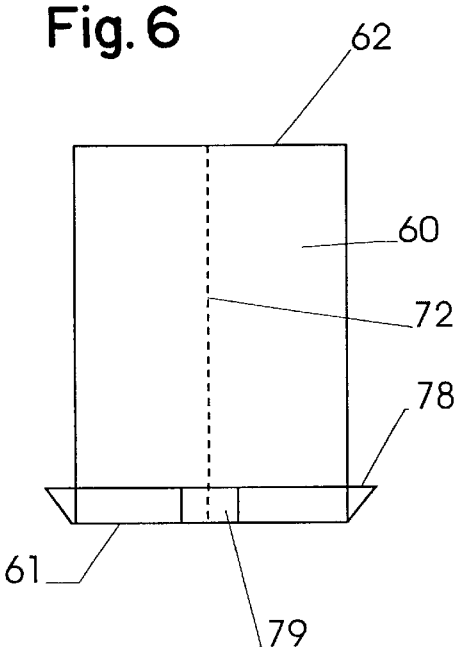
FIG. 6 is a side view of the septum piston.

In operation, when a connection, injection, or aspiration is required, a conventional luer taper cannula 35 having a central opening 94 is inserted into the proximal bore portion 34 of the cylinder 18. Advancement of the luer taper cannula 35 causes longitudinal displacement of the septum piston 60 from within the proximal bore portion 34 into the distal bore portion 38 between the projecting portions 50. This causes compression of the septum 60 in an axis which is aligned with the long transverse axis of the longitudinal slit 72 so that the slit 72 is transversely shortened, and thereby opened to define an open fluid flow channel 100. The formerly cylindrical septum piston 60 is narrowed in one transverse axis and bulges and widens in the perpendicular transverse axis, thereby producing an ellipse with a shortened and now opened central slit 72 (FIG. 2 and FIG. 5), although the actual configuration within the cylinder may be limited in situ by the cylinder wall 46. As noted previously, the projecting members 50 progressively enlarge to progressively narrow the width of the distal portion 38 between the projecting members 50. If the elastomer is soft, this will cause the slit 72 to progressively shorten from its proximal extent toward its distal extent and, therefore, the flow channel 100 will be narrower in the proximal extent and wider toward the distal extent. If the elastomer is comprised of a harder elastomer such as high durometer silicone, for example, exceeding 60 durometer-A medical grade), then the slit 72 will be wedged widely open along its entire length.

After the injection or aspiration is complete, the luer taper cannula 35 is withdrawn from the proximal portion 34 of the cylinder 18. Upon removal of the luer taper cannula 35, the septum piston 60 rebounds gently from its formerly advanced position back into its proximal sealing position with the proximal end of the septum piston returning to a position adjacent the proximal end 30 of the cylinder 18. The lubrication of the septum piston 60 and the progressive narrowing of the opposing members 50 causes the resilient septum piston 60 to rebound back from its advanced position. By using a slowly progressive taper, the force of the rebound can be minimized to prevent kickback of the luer 35 from the proximal portion 34 of the cylinder 18. In addition, an umbrella, as will be discussed, could be attached so as to provide less redundancy and, therefore, to provide elastic rebound. As discussed previously, during the return of the septum piston 60 back toward its resting position, the flow channel 100 can progressively close from its proximal extent to its distal extent to effectively express any liquid contained within the flow channel 100 back toward the main bore 10, rather than out toward the cylinder 18.

It can be seen that, by utilizing the achievement of lateral compression by the application of longitudinal displacing force against the septum piston, the rebound force of the Septum piston is minimized. In other words, despite the fact that the valve is engaged by longitudinal force of the luer taper, the valve is actually opened by lateral compressive force of the cylinder wall or projecting members, rather than the directly applied activating longitudinal force. Therefore, it is not necessary to have a high resisting longitudinal rebound force to achieve and maintain a tight seal. For this reason, it is not necessary for this valve to utilize a deadspace filler of the type described in my U.S. Pat. No. 5,178,607, as will be discussed later. However, the implementation of deadspace displacement or filler provides an opportunity for utilization in valve, septum piston, or piston configurations wherein deadspace is present and wherein it is desirous to eliminate this deadspace so that recapping is not necessary.

Figure 7:
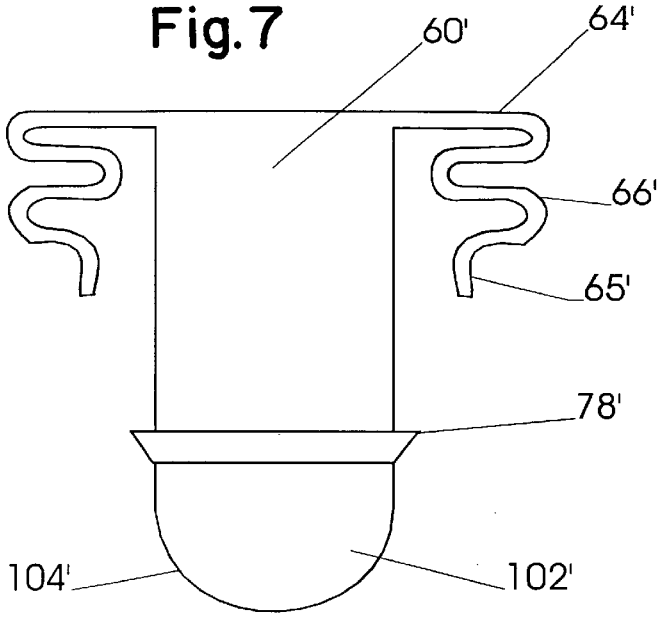
FIG. 7 is a side view of a septum piston having an additional distal portion for occluding the main channel and including a proximal elastic umbrella.

Another similar septum piston embodiment, as shown in FIG. 7, the septum piston 60' can include an integral latex or silicone elastic membranous umbrella 64' which can drape over the outer walls 43 and can be bonded or otherwise securely attached to the outer walls 43 along the umbrella end 65' when the septum piston 60' is inserted into the proximal bore portion 34. This prevents any potential opening at proximal end 30 adjacent inner walls 42 and septum piston 60'. A redundant or bulging umbrella portion 66' may be provided and the umbrella attached distally to allow the redundant portion 66' to be free and to allow less inhibition of longitudinal displacement of the integral septum piston 60' into the distal bore portion 38 during operation.

Figure 8:
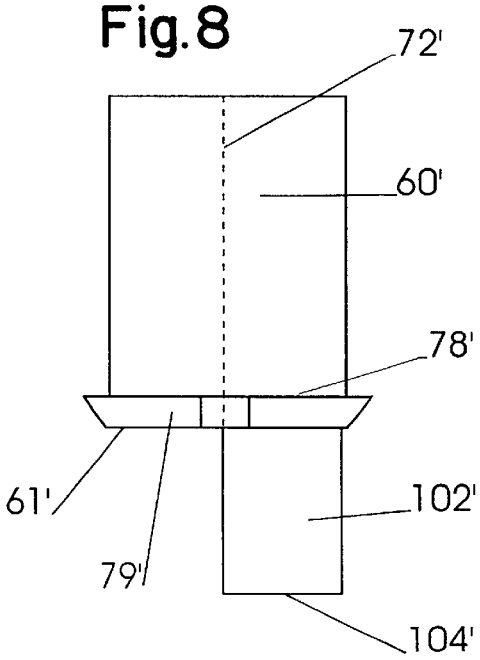
FIG. 8 is a side view of a septum piston showing the distal portion for occluding the main channel.

In another septum piston embodiment (FIGS. 7 and 8), a projecting main bore occluding member 102' is provided adjacent the distal end of the septum piston 60'. The occluding member 102' includes a circular distal end 104' and is sized to be sealingly received into the main bore 10 when the septum piston 60' is advanced. For operation of this embodiment, the cylinder 18 is preferably positioned at an angle relative to the main housing 10 and the secondary bore 22 intersects the main bore 10 at an angle which may be 30°–900° (as in FIG. 1). The main bore 10 is connected distally to a distal conduit which is in fluid connection with a patient's blood vessel. The main bore 10 is connected proximally to a proximal conduit which is in fluid connection with a primary fluid source, such as a high pressure flush bag or a bag of intravenous fluid. The operation of this embodiment is similar to the aforementioned embodiment; however, the occluding member 102' extends distally upon advancement of the septum piston 60' so that the occluding member 102' passes the flow deflector 110' and occludes the main bore 10 adjacent the cylinder 18 in a position intermediate the cylinder 18 and the primary fluid source. This embodiment provides closure of fluid connection between the secondary bore 22 and the primary fluid source, as well as between the patient and the primary fluid source during either aspiration or injection of fluid from the secondary bore 22. This embodiment, therefore, functions to open communication between the opening 94 of the luer 35 and the patient through the septum piston 60' and the main bore 10, while at the same time automatically occluding fluid communication between the primary fluid source and the patient, as well as occluding communication between the primary fluid source and the opening 94 of the luer cannula 35. During injection, this automatically prevents reflux of fluid upstream toward the primary fluid source and assures that the injected fluid is injected toward the patient During aspiration, this assures that aspiration will come from the patient and not from the primary fluid source. The flow deflector 110 can also be sized so that it is engaged by the distal end 61' of the septum piston 60' to prevent excessive advancement of septum piston 60', thereby also functioning as a septum piston stop.

Figure 9:
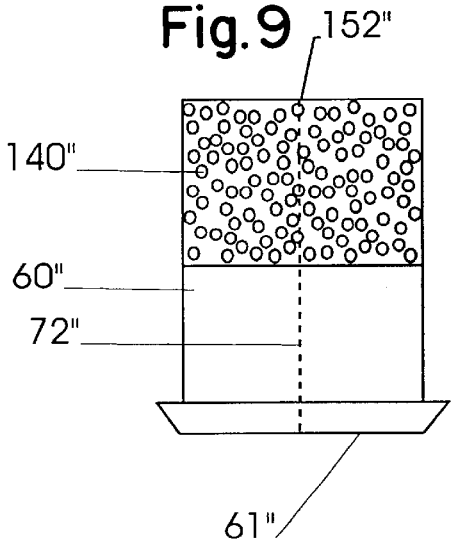
FIG. 9 is another embodiment showing the proximal soft and compressible deadspace filler in association with the septum piston.

In another embodiment (FIG. 9), the septum piston 60" is shorter and a soft deadspace filler 140" is provided. The deadspace filler can be of the type and design for use with very blunt cannulae as discussed in my U.S. Pat. No. 5,178,607 (the disclosure of which is hereby incorporated by reference as if completely disclosed herein). The soft outer filler 140" serves to minimize kickback of the luer taper cannula 35 and functions as a deadspace occluder or displacer. The soft filler 140" can be comprised of foam rubber which can be covered by a medical grade silicone of the type similar to that used in foam cuffs sold by the Bavona Corporation for tracheostomy tubes or can be otherwise constructed to have a similar ease compressibility and relatively low volume in the compressed state and high volume in the resting non-compressed state. The soft portion 140" provides a central perforation 152" for receiving the luer taper cannula 35 through the portion 140" and subsequently into contact with the less easily compressible septum piston 60". Although it is preferred that the two portions be bonded together, they may be separate and the proximal portion may be bonded to the proximal inner walls 42 or the cylinder end 30 or may include an umbrella of the type shown in FIG. 7 or may include another attaching member. As can be seen, the outer soft, easily displaceable filler 140" functions as a deadspace displacer to allow receipt of an extremely blunt cannula, such as a luer taper cannula 35, into a fixed position in relationship with a more stiff and less compressible valve or septum piston 60", the septum piston 60" functions as the actual valve to provide a tight seal and to prevent leakage of even high pressure fluid within the main bore 10. It is the combination of a soft, easily compressible and displaceable outer member 140 in association with a tight sealing lower septum piston or valve 60" which achieves the ability to splint a luer taper cannula 35 in position for reliable engagement with the actual valve mechanism 60", while at the same time allowing for the elimination of deadspace by the soft, easily compressible outer member 140".

It should be clear that alternative configurations of the septum piston are possible within the scope of the present invention. For example, at least a portion of the septum piston may be elliptical in cross-section, with the long transverse axis of the slit aligned with the long axis of the ellipse, and with the projecting septum piston compressing members being aligned with the long axis of the ellipse. This configuration could result in enhanced opening of the slit. The septum piston could be otherwise distorted, either longitudinally or horizontally, in association with longitudinal displacement to achieve an open fluid path. It is, however, preferable that this open fluid path extend through the septum piston and directly in contact with the bore of the luer taper cannula so as to facilitate flow and to absolutely minimize the trapping of fluid or blood within the valve.

Figure 10:
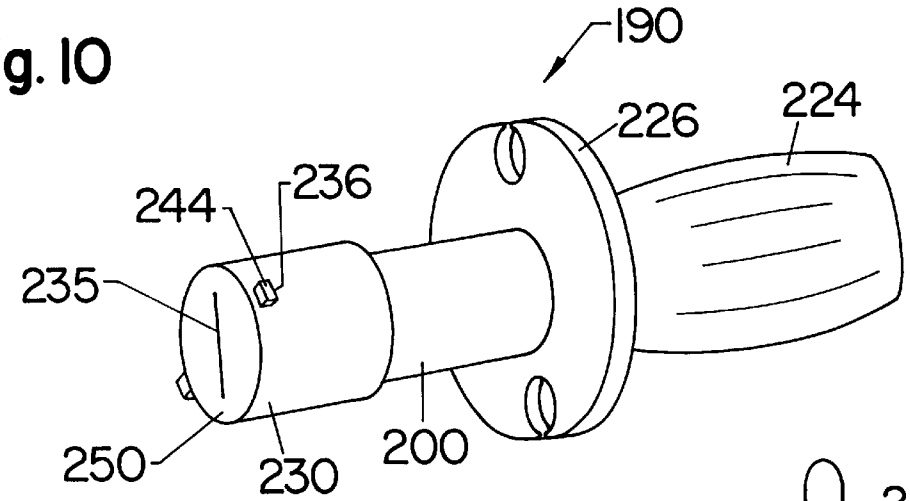
FIG. 10 is a perspective view of a luer tapered cannula protection station.
Figure 11:
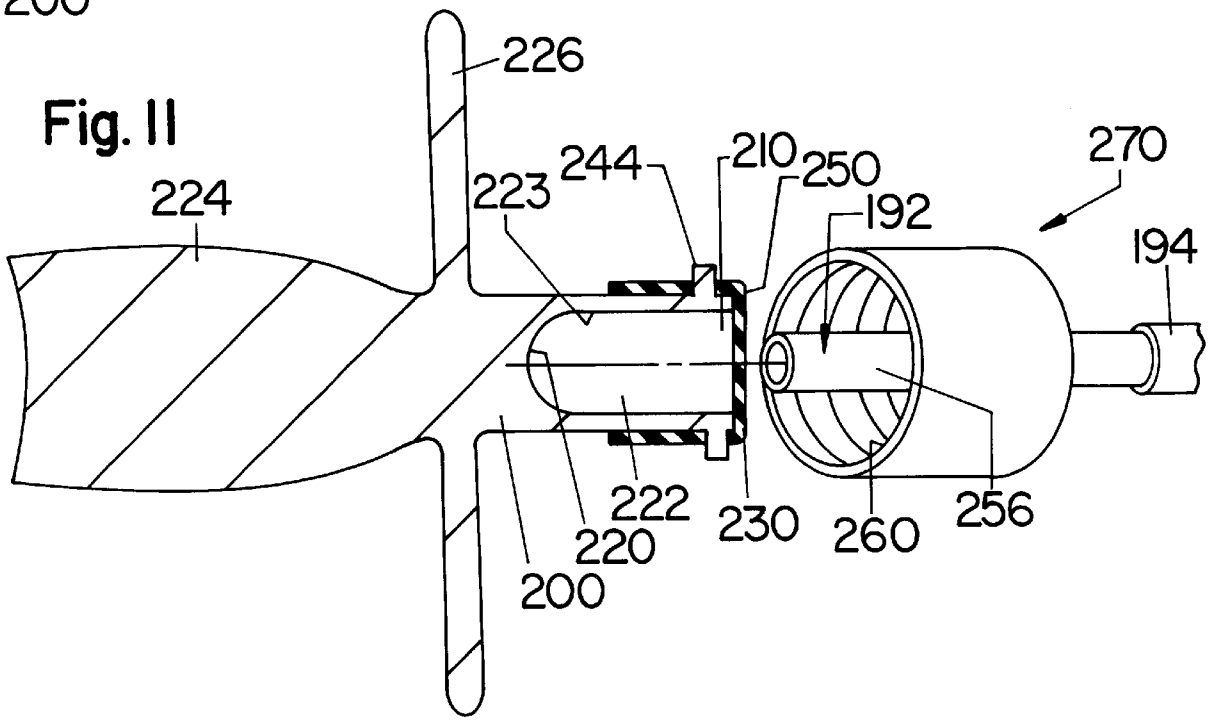
FIG. 11 is a longitudinal section view of a luer tapered cannula protection station showing an adjacent conventional luer lock connector.

FIG. 10 shows a luer taper protecting station 190, which is intended to protect the blunt tapered luer cannula 192 connected to a secondary IV piggyback tubing system 194. The station 190 includes a housing 200 having an open distal end 210 and a closed end 220 defining a chamber 222 having a bore 223. The closed end 220 preferably includes a handle rod 224 and connecting or shield portion 226 for connection to an IV piggyback tubing or the protection station 190 may be otherwise connected along the piggyback system or the pole holding the piggyback system so as to allow easy storage, as discussed in my aforementioned patent. In the preferred embodiment, the open end 210 is occluded by an elastomeric boot 230 which has a closed longitudinal slit 235. The boot is preferably of thin membranous elastomeric material, such as latex rubber or silicone and may be bonded to the housing 200 or otherwise secured. An opening 236 in boot 230 is preferably provided to receive the thread receiving post 244 which is tall enough to threadably engage with the female threading member which is carried by a conventional luer lock connector without disruption of the boot 230. If necessary to prevent the threads of the luer lock from potentially disrupting the boot during threading, two tall posts may be provided on opposite sides of the housing 200. The boot 230, when attached to the distal end of the station 190, produces a distal face 250 which is easily swabbable with antiseptic. As noted, the boot 230 material is preferably membranous elastic and resilient a despite the fact that the male luer taper 192 is close in diameter to the internal transverse dimension of the bore of the station, the elastic boot can be deflected laterally against the inner walls 254 of the station 190 so that even the large diameter of a luer taper 192 can be received within the bore 223 of the station 190 without being inhibited by the low displacement volume and, indeed, easily displaceable elastic boot 230. This is an important feature since there is relatively little clearance between the outer surface 256 of a conventional male tapered luer cannula 192 and the inner surface 260 of the threadable luer lock connector 270 surrounding the taper 192 which must be received over the station 190. It is, therefore, important that the sealing member has a very low displacement or compressed volume so that luer lock connector 270 may be fully received over and through the boot 230 and into the station 190 without the advancement of the cannula 192 fully into the bore 222 being inhibited by the displaced face 250 of boot 230.

Although an elastic membranous boot is shown, a perforated deadspace filler, of the type previously discussed with a compressed low displacement volume, may be used to fill the bore of the station and to receive and cover the luer taper.

It is considered advantageous, as with the present invention, to provide a central perforation and flow channel which will be automatically aligned with the bore of the luer taper, since the end of the luer taper cannula can provide a seal against the upper surface of the septum piston adjacent the perforation to minimize leakage of fluid into the proximal bore portion during operation. It is clear that many modifications may be made to the disclosed embodiment. For example, it can be seen that it is possible for a portion of the distal septum piston to have a fixed relationship to the distal bore portion and for a proximal portion of septum piston to simply compress, rather to be actually displaced. In other words, the septum piston could include a portion which extended into the distal bore portion and which had a fixed relationship to the distal bore portion. In this embodiment, a portion of the septum piston within the proximal bore portion would therefore be compressed into the distal bore portion, despite the fixed position of the distal septum piston within the distal bore portion. In either case, the device functions in a similar manner to achieve longitudinal displacement of at least a portion of the mass of the septum piston along the bore to achieve opening of a centrally-oriented flow channel by lateral compression or otherwise by distorting the septum piston. Although the presently preferred embodiments of this invention have been described, it will be obvious to those skilled in the art that various changes and modifications may be made therein without departing from the invention. Therefore, the claims are intended to include all such changes and modifications which may be made therein without departing from the invention. Therefore, the claims are intended to include all such changes and modifications that fall within the true spirit and scope of the invention.

I claim:

1. A medical valve for selectively providing fluid communication between a primary fluid system and a secondary fluid system, the valve being selectively activated by a male luer having a distal end and an opening therethrough, the valve comprising:

a. a tubular housing defining a longitudinal axis and having a proximal end and a distal end and a bore extending from said proximal end to said distal end, the bore defining a longitudinal axis and having a proximal portion defined by cylindrical walls for receiving a male luer and a distal portion, the distal portion including at least one region having a narrower transverse width than said proximal portion, b. an elastomeric septum piston defining a longitudinal axis and disposed within said bore, said septum piston having a perforation extending along the longitudinal axis of said septum piston, said perforation being closed when said septum piston is free from external compressive force, at least a portion of said septum piston being displaceable along the longitudinal axis of said bore from a first proximal position wherein said perforation is closed to a second distal position wherein said perforation is open, said septum piston being displaced by a distal end of a male luer when a male luer is inserted into said proximal portion, said septum piston in said second distal position being compressed by said region to open said perforation through said septum piston, and thereby to provide fluid communication from said opening, through said septum piston and into a primary fluid system.

2. The valve of claim 1 wherein said perforation is a slit.

3. The medical valve of claim 2 wherein said slit defines a long, transverse axis and wherein said region is defined by at least one projecting member, said member projecting in alignment toward said long transverse axis of said slit so that when at least said portion of said septum piston is longitudinally displaced along said bore and is compressed by said projecting member, said slit being shortened along said transverse axis by said compression so that said slit opens to provide a flow channel through said perforation to provide fluid communication from said open distal luer end through said septum piston.

4. A medical valve for receiving [a] male luer having an open distal end and for selectively providing fluid communication, said valve comprising:

a. a male luer having a distal end and an opening therethrough;

b. a housing having a proximal end and a distal end and a bore, the bore defining a longitudinal axis *and* extending through said housing from said proximal end [to] *toward* said distal end;

c. said housing including a proximal portion for receiving said male luer end and a distal portion;

*d. a compressing member provided in said housing;*

[d] *e. a* [an elastomeric] septum piston*, formed at least in part from elastomeric material,* disposed within said bore, the septum piston being moveable along the longitudinal axis of said [housing] *bore* from a proximal position adjacent said proximal portion to a distal position adjacent said distal portion, the septum piston having a sealed perforation extending through said septum piston, said [distal region] *compressing member* compressing *at least one region of* said septum piston *lateral to said perforation* when said septum piston is displaced by the distal end of said male luer from said proximal position into said distal position, said compression of said septum piston inducing an opening *of said perforation* through said septum piston.

5. The medical valve of claim 4 wherein said septum piston is sized to seal said bore.

6. The medical valve of claim 4 wherein *at least a portion of* said septum piston is generally cylindrical.

7. The medical valve of claim 4 wherein [said compressing portion induces a compressing member,] said compressing member [projecting into] *projects within* said bore.

8. The medical valve of claim 7 wherein said septum piston defines a longitudinal axis and wherein said compressing member compresses *said at least one region of* said septum piston transverse to said longitudinal axis.

9. The medical valve of claim 4, wherein said [region] *compressing member* comprises said bore having a region having variance in maximum dimension transverse to said axis, said septum piston defining a longitudinal axis and a maximum dimension transverse to said axis of said septum and wherein said maximum dimension of said septum piston is greater than the transverse dimension of said bore along said region.

10. The medical valve of claim 4 wherein said [region] *compressing member* comprises said distal portion having a reduced maximum transverse dimension relative to said proximal portion.

11. A medical valve for the transfer of fluid from a fluid receptacle in fluid communication with a connection terminal having an open male end to a tubing system in fluid communication with a patient's blood vessel, the valve comprising:

a. an outer region support housing defining a longitudinal axis;

b. a lumen extending within said outer region support housing, said lumen having an inlet and an outlet;

c. flexible elastomeric occluding member for occluding said inlet, said flexible elastomeric occluding member having an outer face for contact with a male end of a connection terminal and further having a perforation therethrough, said perforation having an upper end adjacent said outer face, at least a portion of said flexible elastomeric occluding member being displaceable along said outer region support housing from a first position wherein said upper end of said perforation is closed to a second position wherein said upper end of said perforation is open;

d. at least one portion of said outer region support housing being sized and configured to narrow said lumen, said at least one portion functioning to compress said flexible elastomeric occluding member, displacement of said flexible elastomeric occluding member inducing compression of said perforation to open said perforation and to provide fluid communication between an open male end of a connection terminal and said outlet.

12. The medical valve of claim 11 wherein said flexible elastomeric occluding member has an elongated portion that is elongated in one dimension transverse to said longitudinal axis.

13. The medical valve of claim 11 wherein said perforation is a slit.

14. The medical valve of claim 11 wherein said outer region support housing includes at least one biasing portion projection from said outer region support housing, said flexible elastomeric occluding member engaging said biasing portion upon displacement of said flexible elastomeric occluding member into said second position to bias said flexible elastomeric occluding member and to thereby open said perforation.

15. A medical valve for selectively providing the communication between a primary fluid system and a secondary fluid system, the valve comprising:

a. a tubular housing defining a longitudinal axis and having a proximal end and a distal end and a bore extending from said proximal end to said distal end, the bore defining a longitudinal axis and having a proximal portion and a distal portion, the distal portion including at least one region having a narrower transverse width than said proximal portion, b. an elastomeric septum piston defining a longitudinal axis and disposed within said bore, said septum piston having a perforation extending along the longitudinal axis of said septum piston, said perforation being closed when said septum piston is free from external compressive force, at least a portion of said septum piston being displaceable along the longitudinal axis of said bore from a first proximal position wherein said perforation is closed, to a second distal position wherein said perforation is open, said septum piston in said distal position being compressed by said region to open said perforation through said septum piston, and thereby to provide fluid communication between the primary and secondary fluid systems through said septum piston.

16. The medical valve of claim 15 wherein said perforation is a slit.

17. The medical valve of claim 16 wherein said slit defines a long, transverse axis and wherein said region is defined by at least one projecting member, said at least one projecting member projecting in alignment toward said long transverse axis of said slit so that when at least a portion of said septum piston is longitudinally displaced along said bore and is compressed by said at least one projecting member, said slit is shortened when so compressed so that said slit opens to provide a flow channel through said perforation.

18. The medical valve of claim 15 wherein said septum piston is generally cylindrical.

19. The medical valve of claim 15 wherein said tubular housing has a generally circular cross-section.

20. A medical valve of claim 1 wherein when the septum piston is in said second distal position, said perforation is substantially free from penetrating structure.

21. A medical valve of claim 4 wherein when the septum piston is in said distal position, said perforation is substantially free from penetrating structure.

22. A medical valve of claim 11 wherein when the septum piston is in said second, position said perforation is substantially free from penetrating structure.

23. A medical valve of claim 15 wherein when the septum piston is in said second distal position, said perforation is substantially free from penetrating structure.

*24. The medical valve of claim 4 wherein said compressing member defines at least one contact portion for engaging and deflecting at least a portion of said septum piston.*

*25. The medical valve of claim 24 wherein said contact portion has a surface inclined with respect to said longitudinal axis.*

*26. The medical valve of claim 25, wherein said surface is inclined toward the longitudinal axis of said bore.*

*27. The medical valve of claim 4 wherein a plurality of compressing members are provided in said housing.*

*28. The medical valve of claim 27 wherein said compressing members are spaced apart in a plane transverse to said longitudinal axis.*

*29. The medical valve of claim 28 wherein at least a portion of said septum piston is forcibly pressed against said compressing member when said septum piston is displaced into said distal position by said male luer.*

*30. The medical valve of claim 27 wherein there are two diametrically opposed compressing members.*

*31. The medical valve of claim 4 wherein at least a portion of a wall of said septum piston engages said compressing member when said septum piston is advanced from said proximal position to said distal position, said compressing member and said wall being sized and configured so that said compressing member exerts a pressing force lateral to said longitudinal axis against said wall to displace at least a portion of said wall when said septum piston is advanced from said proximal position to said distal position thereby inducing dilation opening of said perforation.*

*32. The medical valve of claim 4, wherein said perforation comprises a slit defined between opposing internal walls, said internal walls of said slit contacting each other when said septum piston is in said proximal position and wherein said compressing member and said septum piston are sized and configured such that said internal walls are deflected away from each other by said pressing force when said septum piston is in said distal position.*

*33. The medical valve of claim 32, wherein said slit is substantially free from penetrating structure when said septum piston is in said distal position.*

*34. A medical valve for receiving a male luer end, comprising:*

*a. a housing defining proximal end and a distal end and a bore defining a longitudinal axis and extending*

*through said housing from said proximal end toward said distal end,*

*b. a piston including an elastomeric outer face, said piston being displaceable alone said longitudinal axis from a proximal position to a distal position, said piston in said proximal position being disposed with said face adjacent said proximal end, said piston having a slit extending through said face, said slit defining opposing slit walls, said piston further including at least one elastomeric wall extending generally longitudinally thereof, lateral to said slit walls,*

*c. at least one rigid member positioned adjacent said elastomeric wall and extending generally longitudinally within said housing, said rigid member and said elastomeric wall being sized and configured so that when said piston is advanced along said bore, said rigid member exerts pressing force against at least one region of said elastomeric wall to displace at least a portion of said elastomeric wall in a direction transverse to a longitudinal axis of said slit to thereby separate said slit walls to dilate said slit and to provide fluid communication from said male luer end through said valve.*

*35. The method for selectively providing fluid communication through a medical valve, comprising:*

*providing a male luer having a distal end and an opening therethrough;*

*providing a medical valve including:*

*a housing having a proximal end and a distal end and a bore, the bore defining a longitudinal axis and extending through said housing from said proximal end toward said distal end, said housing including a proximal portion for receiving said male luer end and a distal portion,*

*a septum piston, formed at least in part from elastomeric material, disposed within said proximal portion of said bore, the septum having a sealed slit extending through said septum piston, and*

*a plurality of rigid members disposed in said bore of said housing for engaging a corresponding plurality of portions of said septum piston;*

*contacting a proximal end of said septum piston with said distal end of said male luer;*

*displacing said male luer so as to displace said septum piston in contact therewith along the longitudinal axis of said bore from a proximal position adjacent said proximal portion to a distal position adjacent said distal portion; and*

*applying a compressing force against said portions of said septum piston with said rigid members during said displacing step, thereby opening and dilating said slit, and thereby providing fluid communication through said valve.*

*36. The method of claim 35, wherein said step of providing a medical valve comprises providing a medical valve wherein said rigid members each define at least one wedge portion having a surface inclined with respect to said longitudinal axis.*

*37. The method of claim 36, wherein said compressing step includes forcibly wedging at least a portion of said septum piston about said rigid members when said septum piston is displaced into said distal position by said male luer.*

*38. The medical valve of claim 34 wherein said at least one rigid member and said at least one elastomeric wall are sized and configured such that said compressing force is directed toward said slit when said piston is advanced to said distal position.*

*39. A medical valve for receiving a male luer end, comprising:*

*a. a housing defining a proximal end and a distal end and a bore defining a longitudinal axis and extending through said housing from said proximal end toward said distal end,*

*b. a piston including an elastomeric outer face, said piston being displaceable along said longitudinal axis from a proximal position to a distal position, said piston in said proximal position being disposed with said face adjacent said proximal end, said piston having a slit extending through said face, said slit defining opposing slit walls, said piston further including at least one elastomeric wall extending generally longitudinally, lateral to said slit walls,*

*c. a plurality of rigid members provided within said bore and defining inwardly facing ramps, said rigid members and said piston being sized and configured so that when said piston is advanced along said bore, said rigid members exert a pressing force against a plurality of regions of said piston to transversely displace said regions to thereby separate said slit walls to open said slit and to provide fluid communication from said male luer end through said valve.*

*40. The medical valve of claim 39 wherein said rigid members are integrally formed on an inner wall of said housing defining said bore.*

* * * * *

UNITED STATES PATENT AND TRADEMARK OFFICE

CERTIFICATE OF CORRECTION

PATENT NO. : RE 37,357 E
DATED : September 4, 2001
INVENTOR(S) : Lynn

It is certified that error appears in the above-identified patent and that said Letters Patent is hereby corrected as shown below:

Column 1,
Line 11, insert as follows:
-- Notice: More than one reissue application has been filed for the reissue of patent 5,549,651. The reissue applications are 09/140,413, now U.S. Patent No. Re 37757 (the present application) and 09/699,398, which is a continuation of application 09/140,413 now U.S. Patent No. Re 37357. --

Signed and Sealed this

Fifth Day of April, 2005

JON W. DUDAS
*Director of the United States Patent and Trademark Office*